United States Patent [19]

Satzinger

[11] Patent Number: 5,321,024
[45] Date of Patent: Jun. 14, 1994

[54] ANTIVIRAL PHARMACEUTICAL COMPOSITION FOR TREATING LYMPHOCYTES

[75] Inventor: Gerhard Satzinger, Denzlingen, Fed. Rep. of Germany

[73] Assignee: Godecke Aktiengesellschaft, Berlin, Fed. Rep. of Germany

[21] Appl. No.: 957,590

[22] Filed: Oct. 7, 1992

[30] Foreign Application Priority Data

Oct. 28, 1991 [DE] Fed. Rep. of Germany ....... 4135479

[51] Int. Cl.$^5$ ............................................. A61K 31/54
[52] U.S. Cl. ............................. 514/223.2; 514/223.5
[58] Field of Search ................. 514/223.2, 222.8, 223.5

[56] References Cited

U.S. PATENT DOCUMENTS 4,100,280 7/1978 Dillard et al. .................... 424/246
4,171,361 10/1979 Dillard et al. .................... 424/246

FOREIGN PATENT DOCUMENTS 2335147 1/1975 Fed. Rep. of Germany ......... A61K 31/54
2530792 1/1977 Fed. Rep. of Germany .

OTHER PUBLICATIONS

Abstract 23,434 for FR-M-4 279 (J. Vernin) Published Derwent Abstract Aug. 16, 1966.
Abstract 92-176013/22 for Wo-A-9 208 462 Boehringer Mannheim GmbH Derwent Abstract Published May 21, 1992.
Abstract 09345W-06 for DE-A-2 335 147 (Beiersdorf AG) Derwent Abstract Published Jan. 27, 1977.
Abstract 07856Y/05 for DE-A-2 530 792 (Godecke AG) Derwent Abstract Published Jan. 30, 1975.
Weislow, O. S., et al., *J. Natl. Cancer Inst.*, vol. 81, No. 8, Apr. 19, 1989.

*Primary Examiner*—Marianne M. Cintins
*Assistant Examiner*—Russell Travers
*Attorney, Agent, or Firm*—Elizabeth M. Anderson

[57] ABSTRACT

The present invention provides a pharmaceutical composition containing 3,4-dihydro-1-phenyl-1-thio -1,2,4-benzothiadiazine 1-oxide useful for protecting lymphocytes.

1 Claim, No Drawings

ANTIVIRAL PHARMACEUTICAL COMPOSITION FOR TREATING LYMPHOCYTES

BACKGROUND OF THE INVENTION

The present invention is concerned with a pharmaceutical composition for the treatment of the acquired immune deficiency syndrome (AIDS).

AIDS is an extremely serious disease for which there has not been any therapy leading to a completely successful healing.

German application 25 30 792, covers 3,4-dihydro-1-phenyl-3-thio-1,2,4-benzothiadiazine 1-oxide as an intermediate for the synthesis of benzothiadiazines with hypotensive, spasmolytic, diuretic, and central nervous system-suppressing activities.

Surprisingly, it has now been found that this compound completely protects lymphocytes against attack by HIV viruses and brings about an inhibition of reverse transcriptase.

SUMMARY OF THE INVENTION

The present invention provides a pharmaceutical composition which contains, besides the conventional adjuvants and additives, 3,4-dihydro-1-phenyl-3-thio-1,2,4-benzothiadiazine 1-oxide

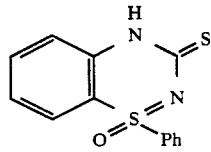

for the protection of lymphocytes of humans and higher mammals, for the inhibition of reverse transcriptase activity, and for the treatment of viral diseases and especially of AIDS.

DETAILED DESCRIPTION

This compound is an agent for treating and/or preventing toxic actions on lymphocytes caused by medicaments or by lymphocytotropic viruses. It is a selective lymphocyte protector.

Lymphocytotoxic medicaments are substances of various classes of active materials: cytostatics, antibiotics, and antihypertensives. These either reduce the number of lymphocytes circulating in the blood or impair their immunological function. Both effects lead to a more or less marked failure of the immune defense which results in an increased susceptibility of the organism to infection. When the number of lymphocytes is reduced, which effect is associated especially with lymphocytopenically-acting cytostatics such as cyclophosphamide, there is, in most cases, an accumulation of immature and immune-incompetent lymphocyte precursors in the bone marrow. At the same time, the number of mature and immune-logically functioning lymphocytes circulating in the blood decreases.

The impairment of immunological function leads, in the case of unchanged lymphocyte count, to a change of the lymphocyte functions. This effect can come about in many different ways. For example, the immune suppressive cyclosporin A inhibits the activation of the actual defensive lymphocytes (cytotoxic T-lymphocytes) via an inhibition of the production of the activating messenger material by the so-called T-helper lymphocytes. Inhibition of the formation of receptors on cytotoxic T-cells to which the activating messenger materials bind is caused by cyclosporin A.

Reversible blocking of these receptors by non-cytotoxic substances provides a protection of the lymphocyte surfaces against lymphocytotropic noxae.

Lymphocytotropic noxae are also to be understood to be lymphocytotropic viruses. The actual infection of the cells by these instigators is first preceded by the binding thereof to certain receptors on the surface of the cell, then the receptor-virus complex is invaginated into the interior of the cell. Lymphocytotropic viruses can either transform the target cells malignly or provoke their elimination by virus-induced autoimmune processes (HIV in the case of T-helper cells). Before the present invention, there has been no effective medication for these lymphocytotropic virus infections. In general, because of the virus-induced massive immune insufficiency, the patients succumb to generalized infections.

Consequently, the particular problem of the lymphocytotropic viruses in comparison with the nonlymphocytotropic viruses is the fact that they preferably infect cells of the immune system and, therefore, cut out precisely the mechanisms which are essential for the elimination of these viruses themselves, as well as of accompanying opportunistic instigators.

It is an object of the present invention to identify substances which are noncytotoxic and are characterized by a great general compatibility, and which displace binding partners of a chemical or viral kind which are toxic for lymphocytes from their specific receptors on lymphocyte surfaces or which prevent their interaction with these target cells via other mechanisms.

In the case of the lymphocytotoxic cytostatics, immune suppression can be prevented by limiting the dosage of these antitumor agents and consequently endanger the patient. Furthermore, the known induction of secondary tumors by cytostatics can also be influenced over a long period of time, the formation of which is favored by the iatrogenic immune deficiency.

Surprisingly, it has now been found that 3,4-dihydro-1-phenyl-3-thio-1,2,4-benzothiadiazine 1-oxide leads to a complete protection of T-lymphocytes against the cytopathic effect of HIV viruses.

In comparative experiments, in in vitro investigations, the following results were found: CPE cell line assay against p24 antigen, $EC_{50} \approx 1.65 \times 10^{-6}$; CEM-IW cell line, $EC_{50} \approx 2 \times 10^{-6}$ inhibition of reverse transcriptase, $IC_{50} = 2$ $\mu M$; comparable values were found for the cell line C8166. This is usually substantially more difficult to protect so, for example, in the case of the use of 3-azide-3'-deoxythymidine (AZT), a 100-fold higher dosage is needed than in the use of the compound of the present invention.

The above assay is described in the *Journal of the National Cancer Institute*, Vol. 81, No. 8, Apr. 19, 1989.

In the case of lymphocytotropic viruses, according to the present invention, the receptors used for the adhesion of instigators to lymphocyte surfaces can be blocked in a nontoxic way. There is considered to be a limited prophylaxis in risk situations but also in the case of already manifest infection, on the basis of the prevention of the infection, there is to be expected over a long period of time a restitution of the immune competence by immune cells provided by the bone marrow. It is then possible to maintain the life of the patient which has hitherto not been possible in the case of HIV infections (AIDS infection).

According to the present invention, 3,4-dihydro-1-phenyl-3-thio-1,2,4-benzothiadiazine 1-oxide can be administered to humans enterally or parenterally in liquid or solid form. As injection medium, aqueous phases are especially used which contain conventional additives, such as stabilizing agents and solubilizing agents. Such additives include, for example, tartrate and citrate buffers, ethanol, complex formers (such as ethylenediamine-tetraacetic acid and the nontoxic salts thereof), as well as high molecular weight polymers (such as liquid polyethylene oxide) for viscosity regulation.

Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats, and solid high molecular weight polymers (such as polyethylene glycols). Compositions suitable for oral administration can, if desired, contain flavoring and/or sweetening agents.

The individual dosage to be administered enterally or parenterally is in the range of from 0.5 to 1000 mg and preferably in the range of from 1 to 100 mg.

EXAMPLE 1

3,4-Dihydro-1-phenyl-3-thio-1,2,4-benzothiadiazine 1-oxide 46.4 g S-(2-amino-phenyl)-S-phenyl-sulfoximide (mp 85° C.) [Chem. Ber. 105, 757 (1972)] is reacted with 80 g carbon disulfide in an autoclave at 170° C. for 24 hours. After cooling, the precipitate is filtered off and washed with ethylacetate. 50 g (91% yield) from methanol/dimethylformamide; mp 280° C.

I claim:

1. A pharmaceutical composition useful for the protection of lymphocytes in a mammal in need of such protection containing, in a pharmaceutically acceptable carrier, a therapeutically effective amount of 3,4-dihydro-1-phenyl-3-thio-1,2,4-benzothiadiazine 1-oxide.

* * * * *